United States Patent [19]

Alpegiani et al.

[11] Patent Number: 5,254,680
[45] Date of Patent: Oct. 19, 1993

[54] PROCESS FOR THE PREPARATION OF 7 ALPHA-ALKOXYCEPHEM DERIVATIVES

[75] Inventors: Marco Alpegiani, Milan; Pierluigi Bissolino, S. Giorgio Lomellina; Matteo D'Anello, Cormano; Ettore Perrone, Boffalora Ticino, all of Italy

[73] Assignee: Farmitalia Carlo Erba S.r.l., Milan, Italy

[21] Appl. No.: 691,089

[22] Filed: Apr. 25, 1991

[30] Foreign Application Priority Data

May 22, 1990 [GB] United Kingdom ................ 9011463

[51] Int. Cl.$^5$ ............................................ C07D 501/04
[52] U.S. Cl. .................................... 540/230; 540/215; 540/228
[58] Field of Search ................. 540/215, 228, 230, 221

[56] References Cited

U.S. PATENT DOCUMENTS

| | | | |
|---|---|---|---|
| 4,093,625 | 6/1978 | Commons | 260/306.7 C |
| 4,456,755 | 6/1984 | Sheehan | 544/23 |
| 4,992,541 | 2/1991 | Blacklick et al. | 540/221 |

FOREIGN PATENT DOCUMENTS

0337704 10/1989 European Pat. Off. .
0411929 2/1991 European Pat. Off. .

OTHER PUBLICATIONS

The Journal of Organic Chemistry, vol. 54, No. 16, Aug. 4, 1989, T. J. Blacklock, et al., "A Versatile Synthesis of 1,1-Dioxo 7-Substituted Cephems: Preparation of the Human Leukocyte Elastase (HLE) Inhibitor 1,1-Dioxo-Trans-7-Methoxycephalosporanic".
James B. Doherty et al., Cephalosporin Antibiotics can be Modified to Inhibit Human Leukocyte Elastase, Nature, vol. 322, Jul. 10, 1986, 192–194, 1 p. formula.
R. J. Bonney et al., Pharmacological Profile of the Substituted Beta-lactam L-659,286: A Member of a New Class of Human PMN Elastase Inhibitors, Journal of Cellular Biochemistry 39:47–53 (1989) Cellular Proteases and Control Mechanisms 7 pages.
William K. Hagmann et al., Inhibition of Human Leukocyte Elastase by C-2 Substituted Cephalosporin Sulfones, J. Med. Chem. 24 (1989) pp. 599–603, Paris.

*Primary Examiner*—Nicholas S. Rizzo
*Attorney, Agent, or Firm*—Oblon, Spivak, McClelland, Maier & Neustadt

[57] ABSTRACT

There is provided a process for preparing a compound of the formula (I):

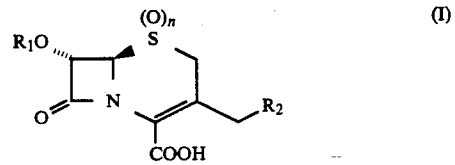

wherein $R_1$ is an organic residue, $R_2$ is a hydrogen or a chlorine atom, a methoxy, ethoxy or an acetoxy group, and n represents 0, 1 or 2.

The process comprises reacting a compound of the formula (II):

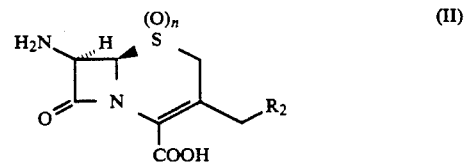

wherein $R_2$ and n are as defined above, with an inorganic or organic nitrite, in an alcohol $R_1OH$, wherein $R_1$ is as defined above, or in a mixture $R_1OH$-organic solvent in the presence of an inorganic or organic acid.

The compounds of the formula (I) are known intermediates in the synthesis of human leucocyte elastase inhibitors (HLE).

17 Claims, No Drawings

PROCESS FOR THE PREPARATION OF 7 ALPHA-ALKOXYCEPHEM DERIVATIVES

The present invention relates to a new process for the preparation of 7α-alkoxycephem derivatives.

It is known that some 7α-alkoxycephen sulphones are potent protease inhibitors, in particular human leucocyte elastase (HLE) inhibitors (see, for example, J. B. Doherty et al., Nature 1986, 322:192; W. K. Hagmann et al., Eur. J. Med. Chem. 1989, 24:599; R. J. Bonney et al., Journal of Cellular Biochemistry, 1989, 39:47).

The 7β-aminocephems, namely 7β-aminocephalosporanic acid (7-ACA) and 7β-amino-3-desacetoxy-cephalosporanic acid (7-ADCA), are the most convenient starting materials for the preparation of 7α-alkoxy cephems. The 7α-alkoxy cephems are useful intermediates in the synthesis of the above mentioned elastase inhibitors and β-lactamase inhibitors, as described in, for example, EP-A-337,704.

The known synthetic sequences for preparing 7α-alkoxy cephems include:
- protection of the $C_4$-carboxylic function of the starting material;
- diazotization to an unstable 7-diazo compound;
- reaction of the 7-diazo compound with the desired alcohol under suitable conditions, especially in the presence of a rhodium catalyst; and
- optionally deprotection of the $C_4$-carboxylic function.

The above mentioned procedure is complex, dangerous and low yielding.

We have found a new, straight forward, simple, safe and high yielding process for transforming 7-ACA, 7-ADCA and their oxidized derivatives (cheap and easily available compounds), into their 7α-alkoxy analogues by a direct conversion in one single step, without using such unstable intermediates as the 7-diazo compounds and without accumulating a hazardous by-product. According to the present invention there is provided a process for preparing a compound of the formula (I):

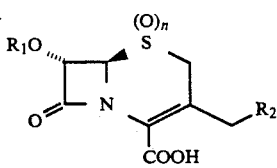

wherein
$R_1$ represents:
(a) a straight or branched alkyl group having from 1 to 20 carbon atoms,
(b) a straight or branched alkenyl group having from 2 to 6 carbon atoms,
(c) a straight or branched alkynyl group having from 2 to 6 carbon atoms, or
(d) an aryl $C_1$–$C_4$ alkyl group such as a phenyl ($C_1$–$C_4$ alkyl) group, each of the groups defined in (a) to (d) above being unsubstituted or substituted by one or more of:
(i) a halogen atom,
(ii) a $C_1$–$C_4$ alkoxy group,
(iii) a cyano group, and
(iv) a $C_1$–$C_4$ alkylthio group,
$R_2$ represents:
1) a hydrogen atom,
2) a chlorine atom,
3) a methoxy or ethoxy group, or
4) an acetoxy group and
n represents zero, one or two;
the process comprises reacting a compound of the formula (II):

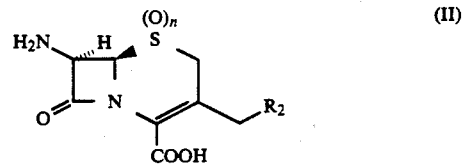

wherein $R_2$ and n are as defined above, with an inorganic or organic nitrite in an alcohol $R_1OH$ wherein $R_2$ is as defined above, or in a mixture of the alcohol $R_1OH$ with an organic solvent, in the presence of an inorganic or organic acid, and optionally converting a resulting compound of the formula (I) wherein n is zero, into a compound of the formula (I) wherein n is one or two by oxidation.

The above mentioned reaction is usually performed at a temperature of from 0° C. to about 60° C.; preferably the reaction is carried out at a temperature of from 10° C. to about 40° C. Moreover, the reaction may be carried out also in the presence of a transition metal catalyst such as, for example, rhodium or copper salts.

$R_1$ preferably, represents:
(a') a straight or branched alkyl group having from 1 to 6 carbon atoms,
(b') a straight or branched alkenyl group having from 2 to 5 carbon atoms,
(c') a straight or branched alkynyl group having from 2 to 4 carbon atoms, or
(d') benzyl,
each of the groups defined in (a') to (d') above, is preferably unsubstituted or substituted by one or more:
(i') chlorine or fluorine atom
(ii') methoxy or ethoxy group,
(iii') cyano group, or
(iv') methylthio group;
$R_2$ preferably represents:
1') a hydrogen atom,
2') a chlorine atom,
3') a methoxy group, or
4') an acetoxy group and
n preferably represents one or two.

More preferably, $R_1$ represents: methyl, ethyl, n-propyl, n-butyl, n-pentyl, n-hexyl, isopropyl, sec-butyl, tert-butyl, allyl, 2-methyl-2-propenyl, 2-butenyl, 3-methyl-2-butenyl, propargyl, 2-butynyl, 2-chloroethyl, 2-fluoroethyl, 2-methoxyethyl, 2-ethoxyethyl, cyanomethyl, 2-methylthiomethyl or benzyl, and $R_2$ represents a hydrogen atom or an acetoxy group.

The inorganic or organic nitrites are preferably of the formula $R_3ONO$ wherein $R_3$ is an alkali metal, an alkaline-earth metal, a $C_1$–$C_6$ alkyl group, an ammonium group or a tetra $C_1$–$C_4$ alkylammonium group.

More preferably $R_3$ is sodium, potassium, butyl, tert-butyl, amyl or tetrabutylammonium.

Preferred inorganic acids are: perchloric acid, sulphuric acid, nitric acid, fluoboric acid, chlorosulfonic acid, boron trifluoride ($BF_3$). Preferred organic acids are sulfonic acids such as, e.g., p-toluenesulfonic acid, methanesulfonic acid, trifluoromethanesulfonic acid.

When the alcohol $R_1OH$ is mixed with an organic solvent, the organic solvent is typically tetrahydrofuran (THF), acetonitrile, dimethoxyethane, hexamethylphosphoramide (HMPA), dimethylformamide (DMF) or N-methylpyrrolidone, preferably THF, DMF or HMPA.

The optional oxidation of a compound of the formula (I) wherein n is zero to give a compound of the formula (I) wherein n is one or two, may be carried out by means of an inorganic or organic peracid or a salt thereof, such as, e.g., peracetic acid, m-chloroperoxybenzoic acid (MCPBA), monoperphthalic acid or monoperoxysulphate acid, usually in a mixture of an inorganic and an organic solvent.

The oxidation preferably is carried out by means of potassium monoperoxysulphate (Oxone®), usually in acetonitrile/water, methanol/water, ethanol/water, dimethylformamide/water or acetone/water; more preferably in acetonitrile/water or methanol/water.

The oxidation is typically carried out at a temperature of from 10° to about 100° C., preferably at a temperature of from 30° to about 70° C.

The starting compounds of the formula II are known compounds or can be prepared from known compounds by known methods. In the formulae of this specification the dotted line ("""") indicates a substituent in the α configuration, i.e. below the plane of the ring, and the wedged line (◄) indicates a substituent in the β configuration, i.e. above the plane of the ring.

The following examples illustrate but do not limit the invention.

EXAMPLE 1

7α-Methoxy-3-methyl-3-cephem-4-carboxylic acid

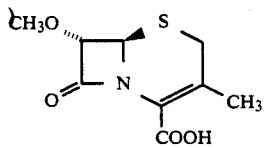

To a solution of 7β-amino-3-desacetoxycephalosporanic acid (7-ADCA)(43 g), 70% perchloric acid (85 ml) and methanol (1400 ml) at room temperature, sodium nitrite (60 g) was added and the resulting mixture was stirred at 25°-270° C. for 6 hours. After pouring into $H_2O$ (1500 ml) and $CH_2C_2$ (800 ml), the organic phase was washed with brine then dried over $Na_2SO_4$ and eventually concentrated to dryness.

The reddish residue was purified by chromathography on LiChroprep® RP18 eluting with water-acetonitrile mixtures. The title compound was obtained as a waxy solid (18.5 g).

NMR (CDCl₃, 90 MHz) δ2.22 (3H, s) 3.37 (2H, ABq, J=18.1 Hz) 3.57 (3H, s) 4,52 (1H,d, J<2 Hz) 4.72 (1H,d J<2 Hz) 8.85 (1H, bs, exch. with D₂O).

IR (CHCl₃)δmax 1775, 1725 cm⁻¹.

EXAMPLE 2

By following a procedure similar to that described in example 1 and substituting the proper alcohol for the methanol as reaction solvent, the below reported compounds were prepared:

7α-Ethoxy-3-methyl-3-cephem-4-carboxylic acid

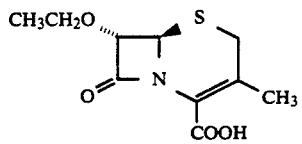

NMR (CDCl₃+D₂O, 200 MHz), δ1.27 (6H, , J=7.0 Hz), 2.21 (3H, s), 3.21 (1H,d, J=18.3 Hz), 3.54 (1H, dd, J=0.9 and 18.3 Hz), 3.6-3.9 (4H, m), 4.54 (1H,d, J=1.5 Hz), 4.68 (1H, d, J=1.5 Hz).

IR (CHCl₃)δmax 1770, 1725 cm⁻¹;

7α-Isopropoxy-3-methyl-3-cephem-4-carboxylic acid

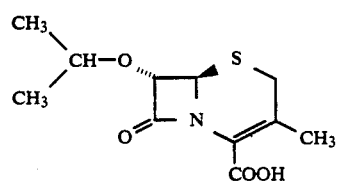

NMR (CDCl₃+D₂O, 200 NHz) δ1.26 (3H, d, J=6.2 Hz) 2.21 (3H, s) 3.20 (1H, d, J=18.1 Hz) 3.54 (1H, dd, J=0.9 and 18.1 Hz) 3.82 (1H, m) 4.52 (1H, d, J=1.6 Hz) 4.61 (1H, d, J=1.6 Hz).

IR (CHCl₃)δmax 1780, 1725 cm⁻¹;

7α-Butoxy-3-methyl-3-cephem-4-carboxylic acid

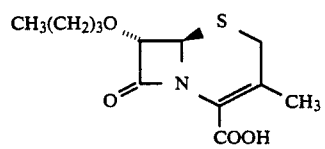

NMR (CDCl₃+D₂O, 200 MHz) 0.92 (3H, t, J=7.2 Hz) 1.3-1.5 (2H, m) 1.5-1.8 (2H, m) 2.22 (3H, s) 3.23 (1H, d, J=18.1 Hz) 3.53 (1H, dd, J=1 Hz and 18.1 Hz) 3.5-3.8 (2H, m) 4.56 (1H,d, J=1.6 Hz) 4.69 (1H,d, J=1.6 Hz)

IR (CHCl₃)δmax 1780, 1725, cm⁻¹;

7α-(2-Methoxyethoxy)-3-methyl-3-cephem-4-carboxylic acid

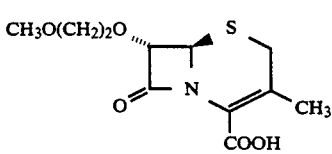

NMR (CDCl₃+D₂O, 200 NHz) δ2.20 (3H, s) 3.19 (1H, d, J=18.1 Hz) 3.39 (3H, S) 3.52 (1H, d, J=18.1 Hz) 3.5-4.0 (4H, m) 4.61 (1H,d, J=1.5 Hz) 4.72 (1H,d, J=1.5 Hz)

IR (CHCl₃)δmax 1785, 1720 cm⁻¹;

7α-Allyloxy-3-methyl-3-cephem-4-carboxylic acid

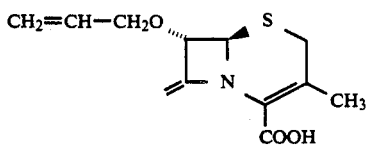

NMR (CDCl₃+D₂O, 200 NMz) δ2.20 (3H,s) 3.20 (1H,d,J=18.2 Hz) 3.53 (1H,d, J=18.2 Hz) 4.0–4.4 (2H,m) 4.57 (1H,d, J=1.6 Hz) 4.68 (1H,d, J=1.6 Hz) 5.29 (1H, dd, J=1.1 and 10.2 Hz) 5.36 (1H, dd, J=1.4 and 7.1 Hz) 5.8–6.0 (1H,m).

IR (CHCl₃)δmax 1775 and 1725 cm⁻¹.

EXAMPLE 3

7α-Methoxy-3-acetoxvinethyl-3-cephem-4-carboxylic acid

By following a procedure similar to that described in Example 1 and using 7β-aminocephalosporanic acid (7-ACA) instead of 7β-amino-3-desacetoxycephalosporanic acid (7-ADCA) the title compound was obtained as a white solid.

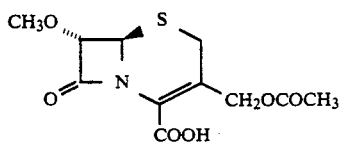

IR (CHCl₃) 1785, 1740–1720 cm⁻¹.

EXAMPLE 4

7α-Methoxy-3-methyl-3-cephem-4-carboxylic acid 1,1-dioxide

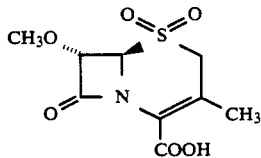

A mixture of 7β-amino-3-desacetoxycephalosporanic acid (43 g), 70% perchloric acid (80 ml), reethanol (1300 ml) and sodium nitrite (45 g) was stirred at 250° for 6 hours, then poured into H₂O/CH₂Cl₂. The organic phase was washed with brine, then concentrated in vacuo.

The residue was taken up with acetonitrile (300 ml) and water (300 ml). Oxone ® (potassium peroxymonosulfate) (90 g) was added and the mixture was heated at 550° for 2 hours under stirring. The mixture was filtered and the filtrate was poured into H₂O/ethyl acetate. The organic phase was washed with brine then concentrated under vacuum.

Treatment of the residue with diethyl ether allowed the isolation of the title compound as white crystals (12 g).

IR (KBr) 1788, 1731 cm⁻¹.

EXAMPLE 5

7α-methoxy-3-methyl-3-cephem-4-carboxylic acid-1,1-dioxide

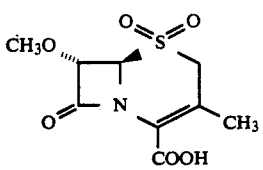

Step a

A solution of tert-butyl 7β-amino--3-denacetoxycephalosporate (25 g) in dichloromethane/dioxane 1:1 (600 ml) was treated with tert-butyl percarbonate (32.7 g) and triethylamine (14 ml). After standing overnight at room temperature, the solution was concentrated and the residue was purified by flash chromatography, affording tert-butyl 7β-tert-butoxycarbonylamino-3-desacetoxycephalosporanate (27 g) as 3:1 mixture of Δ³ and Δ² isomers.

This product was dissolved in dichloromethane (400 ml) and treated at −10° C. with 55% MCPBA (65 g), then stirred 6 hours at room temperature. The mixture was filtered and the filtrate washed sequentially with 4% aq. NaHSO₃, 4% aq. NaHCO₃ and sat. aq. NaCl solutions. The organic phase was dried over Na₂SO₄ and concentrated in vacuo.

The residue was treated with diethyl ether affording tert-butyl 7β-tert-butoxycarbonyl-3-desacetoxycephalosporate 1,1-dioxide (Δ³ isomer) as white crystals (30 g). This compound (11 g) was dissolved in dichloromethane (50 ml) and treated with anisole (10 ml) and trifluoroacetic acid (100 ml) for 3 hours at room temperature. The mixture was concentrated under vacuum to a small volume, then treated with diethyl ether.

A yellowish solid was formed, which was filtered and washed with diethyl ether; it was then poured into water (300 ml). The pH value was adjusted to 4 by adding NAHCO₃ portionwise. After stirring at pH 4 for 1 hour at 10° C., the mixture was filtered and the white solid washed with water then acetone. After drying under vacuum, there were obtained as a white powder 5.5 g of 7β-amino-3-desacetoxycephalosporanic acid sulphone.

IR (KBr) 1810, 1640, 1550 cm⁻¹.

NMR (200 MHz, CF₃COOD)δ2.33 (3H,S) 4.12 (1H,d,J=18.7 Hz) 4.28 (1H,d,J=18.7 Hz) 5.37 (1H,d,J=4.6 Hz) 5.63 (1H,d,J=4.6 Hz).

Step b

To a stirred solution of 7β-amino-3-desacetoxycephalosporanic acid sulphone (2.5 g) in methyl alcohol (70 ml) and 70% HClO₄ (2 ml) at 20° C., sodium nitrite (3 g) was added.

The resulting mixture was stirred at room temperature for 4 hours, then poured into water/ethyl acetate.

The organic phase was dried over NA₂SOH₄ and concentrated in vacuo.

Purification of the residue by reversed-phase chromatography (Lichroprep ® RP 18) eluting with water/acetonitrile mixtures allowed the isolation of the title product as a white powder (450 mg).

NMR (DMSO-d₆)δ1.91 (3H,s) 3.52 (3H,s) 4.20 (2H,s) 5.13 (1H,d,J=1.2 Hz) 5.35 (1H,s).

EXAMPLE 6

7α-methoxy-3-methyl-3-cephem-4-carboxylic acid

To a solution of 7β-amino-3-degacetoxycephalosporanic acid (4.3 g), methanesulphonic acid (3.88 ml) and reethanol (140 ml) at room temperature, potassium nitrite (3.5 g) was added and the resulting mixture was stirred for 12 hours at room temperature. The reaction mixture was worked up as described in Example 1 affording the title product as a colourless oil (1.6 g) which solidified in the fridge.

IR $(CHCl_3)\delta$max 1775, 1725 cm$^{-1}$.

EXAMPLE 7

7α-methoxy-3-methyl-3-cephem-4-carboxylic acid

7β-Amino-3-desacetoxycephalosporanic acid (7-ADCA) (5.25 g) was added to a solution of boron trifluoride etherate ($d^{20}$ 1.13; 22 ml) in methanol (170 ml) at 10° C. After 1 min. sodium nitrite ($NaNO_2$) (5.0 g) was added and the resulting mixture was stirred for 12 h at 150° C., then poured into $CH_2Cl_2$/water. The organic phase was dried ($Na_2SO_4$) and concentrated "in vacuo".

The crude product was purified by ion-exchange chromatography (Amberlite IRA-458, elution with pH 7 phosphate buffer).

The product containing fractions (HPLC monitoring) were salted with NaCl, acidified with 20% aqueous HCl and extracted with ETOAC.

After evaporation of the dried ETOAC solution, the title product was obtained as a waxy solid (3.2 g) with the same physics-chemical characteristics of the compound prepared in Example 1.

EXAMPLE 8

7α-methoxy-3-methyl-3-cephem-4-carboxylic acid 1,1-dioxide

96% $H_2SO_4$ (15 ml) was slowly added to a mixture of 7-ADCA (10.5 g) in methanol (350 ml) while keeping the temperature under 0° C. Sodium nitrite ($NaNO_2$) (15 g) was then added and the mixture was stirred for 15 h at 180° C. After pouring into ETOAc/water, the organic phase was dried ($Na_2SO_4$) and rotoevaporated.

The residue (10 g) was dissolved in acetonitrile (200 ml) and water (200 ml). Potassium monoperoxy sulphate (Oxone ®) (50 g) was then carefully added, and the mixture was heated at 55° C., under vigorous stirring, for 1.5 h; the reaction mixture was poured into ETOAc/water. The organic phase was washed with aqueous $NAHSO_3$ then brine and eventually it was dried and concentrated. The residue was taken up with diethyl ether - diisopropyl ether and let stand at 4° C. overnight.

The title product obtained as a white solid (4.1 g) showed the same physics-chemical characteristics of the compound prepared in Example 5.

We claim:

1. A process for the preparation of a compound of the formula (I):

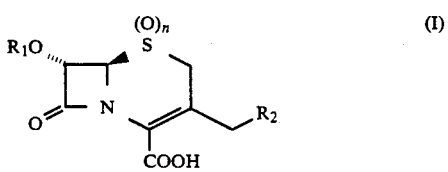

wherein
R$_1$ represents:
 (a) a straight or branched alkyl group having from 1 to 20 carbon atoms,
 (b) a straight or branched alkenyl group having from 2 to 6 carbon atoms,
 (c) a straight or branched alkynyl group having from 2 to 6 carbon atoms, or
 (d) an aryl C$_1$-C$_4$ alkyl group,
 each of the groups defined in (a) to (d) above being unsubstituted or substituted by one or more of:
 (i) a halogen atom,
 (ii) a C$_1$-C$_4$ alkoxy group,
 (iii) a cyano group, and
 (iv) a C$_1$-C$_4$ alkylthio group,
R$_2$ represents:
 1) a hydrogen atom,
 2) a chlorine atom,
 3) a methoxy or ethoxy group, or
 4) an acetoxy group and
n represents zero, one or two;
the process comprising reacting a compound of the formula (II):

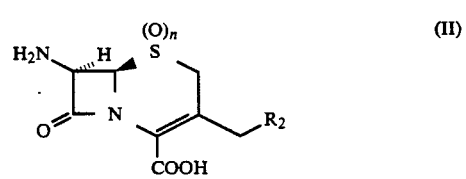

wherein R$_2$ and n are as defined above, with an inorganic or organic nitrite in an alcohol R$_1$OH wherein R$_1$ is as defined above, or in a mixture of the alcohol R$_1$OH with an organic solvent, in the presence of an inorganic or organic acid.

2. A process according to claim 1 wherein R$_1$ is:
 (a') a straight or branched alkyl group having from 1 to 6 carbon atoms,
 (b') a straight or branched alkenyl group having from 2 to 5 carbon atoms,
 (c') a straight or branched alkynyl group having from 2 to 4 carbon atoms, or
 (d') benzyl,
each of the groups defined in (a') to (d') above, being unsubstituted or substituted by one or more:
 (i') chlorine or fluorine atom
 (ii') methoxy or ethoxy group,
 (iii') cyano group, or
 (iv') methylthio group.

3. A process according to claim 1 or 2 wherein R$_1$ is methyl, ethyl, n-propyl, n-butyl, n-pentyl, n-hexyl, isopropyl, sec-butyl, tert-butyl, allyl, 2-methyl-2-propenyl, 2-butenyl, 3-methyl-2-butenyl, propargyl, 2-butynyl, 2-chloroethyl, 2-fluoroethyl, 2-methoxyethyl, 2-ethoxyethyl, cyanomethyl, 2-methylthionethyl or benzyl.

4. A process according to claim 1 or 2 wherein R$_2$ is:
 1') a hydrogen atom,
 2') a chlorine atom,
 3') a methoxy group, or
 4') an acetoxy group.

5. A process according to claim 4 wherein R$_2$ is a hydrogen atom or an acetoxy group.

6. A process according to claim 1 or 2 wherein n is one or two.

7. A process according to claim 1 or 2 which the inorganic or organic nitrite is of the formula R$_3$NO wherein $R_3$ is an alkali metal, an alkaline-earth metal, a $C_1$–$C_6$ alkyl group, an ammonium group or a tetra($C_1$–$C_4$ alkyl)ammonium group.

8. A process according to claim 7 wherein $R_3$ is sodium, potassium, butyl, tertbutyl, amyl or tetrabutylannonium.

9. A process according to claim 1 or 2 wherein the inorganic acid is perchloric acid, sulphuric acid, nitric acid, fluoboric acid, chlorosulfonic acid or boron trifluoride.

10. A process according to claims 1 or 2 wherein the organic acid is a sulfonic acid.

11. A process according to claim 10 wherein the sulfonic acid is p-toluenesulfonic acid, methanesulfonic acid or trifluoromethanesulfonic acid.

12. A process according to claim 1 or 2 wherein the reaction is carried out at a temperature of from 0° C. to 600° C.

13. A process according to claim 12 wherein the reaction is carried out at a temperature of from 10° to 40°.

14. A process according to claim 1 or 2 in which the final conversion of a compound of the formula (I) wherein n is zero into a compound of the formula (I) wherein n is one or two is carried out with potassium monoperoxysulphate in a mixed organic-inorganic solvent.

15. A process according to claim 14 wherein the mixed organic-inorganic solvent is acetonitrile/water, methanol/water, ethanol/water, dimethylformamide/water or acetone/water.

16. A process according to claim 1 or 2 wherein the oxidation of a compound of formula (I) wherein n is zero into a corresponding compound of formula (I) in which n is one or two is carried out at a temperature of from 30° C. to 700° C.

17. A process according to claim 1 wherein a resultant compound of the formula (I) wherein n is 0, is converted into a compound of the formula (I) wherein n is 1 or 2 by oxidation.

* * * * *

UNITED STATES PATENT AND TRADEMARK OFFICE
CERTIFICATE OF CORRECTION

PATENT NO. : 5,254,680

DATED : October 19, 1993

INVENTOR(S) : Marco Alpegiani, et. al.

It is certified that error appears in the above-indentified patent and that said Letters Patent is hereby corrected as shown below:

On the title page, [57] Abstract, last line, "elastase inhibitors (HLE)" should read --elastase (HLE) inhibitors--

Column 1, line 56, "f rom" should read --from--;

line 58, "f rom" should read --from--.

Column 3, line 50, "25°-270°C" should read --25°-27°C--;

line 51, "$CH_2C_2$" should read --$CH_2Cl_2$--;

lines 58-60, "NMR($CDCl_3$, 90 MHz) δ2.22 (3H,s) 3.37 (2H, ABq, J=18.1 Hz) 3.57 (3H,s) 4,52 (1H,d,J<2 Hz) 4.72 (1H,d J<2 Hz) 8.85 (1H, bs, exch. with $D_2O$)" should read --NMR($CDCl_3$, 90 MHz)δ 2.22 (3H,s), 3.37 (2H, ABq, J=18.1 Hz), 3.57 (3H,s), 4,52 (1H,d,J<2 Hz), 4.72 (1H,d J<2 Hz), 8.85 (1H, bs, exch. with $D_2O$)--;

UNITED STATES PATENT AND TRADEMARK OFFICE
CERTIFICATE OF CORRECTION

PATENT NO. : 5,254,680
DATED : October 19, 1993
INVENTOR(S) : Marco Alpegiani, et. al.

It is certified that error appears in the above-indentified patent and that said Letters Patent is hereby corrected as shown below:

Column 3, line 61, "$\delta$max" should read --$\nu$max--.

Column 4, line 12 "NMR(CDCl$_3$+D$_2$O, 200 MHz),$\delta$1.27 (6H,,J=7.0" should read --NMR(CDCl$_3$+D$_2$O, 200 MHz), $\delta$ 1.27 (3H,,J=7.0--;

line 14, "J=0.9 and 18.3 Hz), 3.6-3.9 (4H,m), 4.54 (1H,d,J=1.5" should read --J=0.9 and 18.3 Hz), 3.6-3.9 (2H,m), 4.54 (1H,d,J=1.5-- line 16, "$\delta$Max" should read --$\nu$max--;

lines 29-32, "NMR (CDCl$_3$+D$_2$O, 200 NHz) $\delta$1.26 (3H,d,J=6.2 Hz) 2.21 (3H,s) 3.20 (1H,d,J=18.1 Hz) 3.54 (1H,dd,J=0.9 and 18.1 Hz) 3.82 (1H,m) 4.52 (1H,d,J=1.6 Hz) 4.61 (1H,d,J=1.6 Hz)" should read --NMR (CDCl$_3$+D$_2$O, 200 MHz) $\delta$ 1.22 and 1.26 (6M, two t, J=6.2 Hz), 1.26 (3H,d,J=6.2 Hz), 2.21 (3H,s),

UNITED STATES PATENT AND TRADEMARK OFFICE
CERTIFICATE OF CORRECTION

PATENT NO. : 5,254,680

DATED : October 19, 1993

INVENTOR(S) : Marco Alpegiani, et. al.

It is certified that error appears in the above-indentified patent and that said Letters Patent is hereby corrected as shown below:

3.20 (1H,d,J=18.1 Hz), 3.54 (1H,dd,J=0.9 and 18.1 Hz), 3.82 (1H,m), 4.52 (1H,d,J=1.6 Hz), 4.61 (1H,d,J=1.6 Hz)--;

Column 4, line 33, "$\delta$max" should read --$\nu$max--;

lines 45-49, "NMR ($CDCl_3+D_2$, 200 MHz) 0.92 (3H,t,J=7.2 Hz) 1.3-1.5 (2H,m) 1.5-1.8 (2H,m) 2.22 (3H,s) 3.23 (1H,d,J=18.1 Hz) 3.53 (1H,dd,J=1 Hz and 18.1 Hz) 3.5-3.8 (2H,m) 4.56 (1H,d,J=1.6 Hz) 4.69 (1H,d,J=1.6 Hz)" should read --NMR ($CDCl_3+D_2$, 200 MHz) $\delta$ 0.92 (3H,t,J=7.2 Hz), 1.3-1.5 (2H,m), 1.5-1.8 (2H,m), 2.22 (3H,s), 3.23 (1H,d,J=18.1 Hz), 3.53 (1H,dd,J=1 Hz and 18.1 Hz), 3.5-3.8 (2H,m), 4.56 (1H,d,J=1.6 Hz), 4.69 (1H,d,J=1.6 Hz).--;

line 50, "$\delta$max" should read --$\nu$max--;

UNITED STATES PATENT AND TRADEMARK OFFICE
CERTIFICATE OF CORRECTION

PATENT NO. : 5,254,680

DATED : October 19, 1993

INVENTOR(S) : Marco Alpegiani, et. al.

It is certified that error appears in the above-indentified patent and that said Letters Patent is hereby corrected as shown below:

Column 4, lines 63-66, "NMR ($CDCl_3+D_2O$, 200 NHz) $\delta$2.20 (2H,s) 3.19 (1H,d,J=18.1 Hz) 3.39 (3H,S) 3.52 (1H,d,J=18.1 Hz) 3.5-4.0 (4H,m) 4.61 (1H,d,J=1.5 Hz) 4.72 (1H,d,J=1.5 Hz)" should read --NMR ($CDCl_3+D_2O$, 200 NHz) $\delta$ 2.20 (2H,s), 3.19 (1H,d,J=18.1 Hz), 3.39 (3H,s), 3.52 (1H,d,J=18.1 Hz), 3.5-4.0 (4H,m), 4.61 (1H,d,J=1.5 Hz), 4.72 (1H,d,J=1.5 Hz).--;

line 67, "$\delta$max" should read --$\nu$max--.

Column 5, line 5,

"
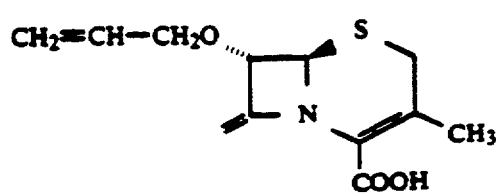
"

UNITED STATES PATENT AND TRADEMARK OFFICE
CERTIFICATE OF CORRECTION

PATENT NO. : 5,254,680
DATED : October 19, 1993
INVENTOR(S) : Marco Alpegiani, et. al.

It is certified that error appears in the above-indentified patent and that said Letters Patent is hereby corrected as shown below:

should read

--

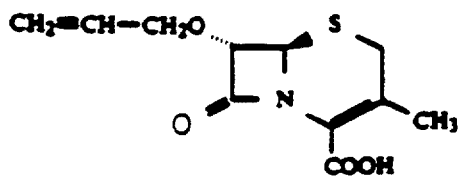

--;

Column 5, lines 10-14, "NMR (CDCl$_3$+D$_2$O, 200 NMz) δ2.20 (3H,s) 3.20 (1H,d,J=18.2 Hz) 3.53 (1H,d, J=18.2 Hz) 4.0-4.4 (2H,m) 4.57 (1H,d,J=1.6 Hz) 4.68 (1H,d,J=1.6 Hz) 5.29 (1H,dd,J=1.1 and 10.2 Hz) 5.36 (1H,dd,J=1.4 and 7.1 Hz) 5.8-6.0 (1H,m)" should read

UNITED STATES PATENT AND TRADEMARK OFFICE
CERTIFICATE OF CORRECTION

PATENT NO. : 5,254,680
DATED : October 19, 1993
INVENTOR(S) : Marco Alpegiani, et. al.

It is certified that error appears in the above-indentified patent and that said Letters Patent is hereby corrected as shown below:

--NMR (CDCl$_3$+D$_2$O, 200 NMz) δ 2.20 (3H,s), 3.20 (1H,d,J=18.2 Hz), 3.53 (1H,d, J=18.2 Hz), 4.0-4.4 (2H,m), 4.57 (1H,d,J=1.6 Hz), 4.68 (1H,d,J=1.6 Hz), 5.29 (1H,dd,J=1.2 and 10.2 Hz), 5.36 (1H,dd,J=1.2 and 7.1 Hz), 5.8-6.0 (1H,m)--;

Column 5, line 17, "δmax" should read --νmax--;

line 20, "7α-Methoxy-3-acetoxvinethyl-3-cephem-4-carboxylic" should read --7α-Methoxy-3-acetoxymethyl-3-cephem-4-carboxylic--;

line 36, "IR (CHCl$_3$) 1785" should read --IR (CHCl$_3$) νmax 1785--;

line 51, "reethanol" should read --methanol--;

line 52, "250°" should read --25°C--;

UNITED STATES PATENT AND TRADEMARK OFFICE
CERTIFICATE OF CORRECTION

PATENT NO. : 5,254,680
DATED : October 19, 1993
INVENTOR(S) : Marco Alpegiani, et. al.

It is certified that error appears in the above-indentified patent and that said Letters Patent is hereby corrected as shown below:

Column 5, line 60, "550°" should read --55°C--;

line 68, "IR (KB$_r$) 1788" should read --IR (KB$_r$) $\nu$max 1788--.

Column 6, line 3, "7α-methoxy-3-methyl-3-cephem-4-carboxylic" should read --7α-Methoxy-3-methyl-3-cephem-4-carboxylic--;

line 16, "-3-denacetoxycephalosporate" should read -- -3-desacetoxycephalosporandie--;

line 43, "NAHCO$_3$" should read --NaHCO$_3$--;

line 49, "IR (KBr) 1810" should read --IR (KBr) $\nu$max 1810--;

lines 50-52, "NMR (200 MHz, CF$_3$COOD)δ2.33 (3H,S) 4.12 (1H,d,J=18.7 Hz) 4.28 (1H,d,J=18.7 Hz) 5.37 (1H,d,J=4.6 Hz) 5.63 (1H,d,J=4.6 Hz)" should read

UNITED STATES PATENT AND TRADEMARK OFFICE
CERTIFICATE OF CORRECTION

PATENT NO. : 5,254,680

DATED : October 19, 1993

INVENTOR(S) : Marco Alpegiani, et. al.

Page 8 of 11

It is certified that error appears in the above-indentified patent and that said Letters Patent is hereby corrected as shown below:

--NMR (200 MHz, $CF_3COOD$) $\delta$ 2.33 (3H,s), 4.12 (1H,d,J=18.7 Hz), 4.28 (1H,d,J=18.7 Hz), 5.37 (1H,d,J=4.6 Hz), 5.63 (1H,d,J=4.6 Hz)--;

Column 6, line 61, "$NA_2SOH_4$" should read --$Na_2SO_4$--;

lines 67-68, "NMR (DMSO-$d_6$)$\delta$1.91 (3H,s) 3.52 (3H,s) 4.20 (2H,s) 5.13 (1H,d,J=1.2 Hz) 5.35 (1H,s)" should read --NMR (DMSO-$d_6$)$\delta$ 1.91 (3H,s), 3.52 (3H,s), 4.20 (2H,bs), 5.13 (1H,d,J=1.2 Hz), 5.35 (1H,bs)--.

Column 7, line 2, "7$\alpha$-methoxy-3-methyl-3-cephem-4-carboxylic acid" should read --7$\alpha$-Methoxy-3-methyl-3-cephem-4-carboxylic acid--;

line 4, "7$\beta$-amino-3-degacetoxycephalosporanic" should read --7$\beta$-amino-3-desacetoxycephalosporanic--

UNITED STATES PATENT AND TRADEMARK OFFICE
CERTIFICATE OF CORRECTION

PATENT NO. : 5,254,680
DATED : October 19, 1993
INVENTOR(S) : Marco Alpegiani, et. al.

It is certified that error appears in the above-indentified patent and that said Letters Patent is hereby corrected as shown below:

Column 7, line 6, "reethanol" should read --methanol--;

line 12, "IR (CHCl$_3$)δmax 1775" should read --IR(CHCl$_3$) νmax 1775--;

line 15, "7α-methoxy-3-methyl-3-cephem-4-carboxylic acid" should read --7α-Methoxy-3-methyl-3-cephem-4-carboxylic acid";

line 22, "150° C" should read --15°C--;

line 29, "ETOAC" should read --ETOAc--;

line 30, "ETOAC" should read --ETOAc--;

line 32, "physics-chemical" should read --physico-chemical--;

line 36, "7α-methoxy-3-methyl-3-cephem-4-carboxylic acid" should read --7α-Methoxy-3-methyl-3-cephem-4-carboxylic acid--;

UNITED STATES PATENT AND TRADEMARK OFFICE
CERTIFICATE OF CORRECTION

PATENT NO. : 5,254,680
DATED : October 19, 1993
INVENTOR(S) : Marco Alpegiani, et. al.

It is certified that error appears in the above-indentified patent and that said Letters Patent is hereby corrected as shown below:

Column 7, line 42, "180° C" should read --18°C--;

line 50, "NAHSO$_3$" should read --NaHSO$_3$--;

line 55, "physics-chemical" should read --physico-chemical--.

Column 8, line 57, "2-methylthionethyl" should read --2-methylthiomethyl--.

Column 9, lines 6-7, "tetrabutylan-nonium" should read --tetrabutylam-monium--;

line 22, "600° C" should read --60° C--.

UNITED STATES PATENT AND TRADEMARK OFFICE
CERTIFICATE OF CORRECTION

PATENT NO. : 5,254,680
DATED : October 19, 1993
INVENTOR(S) : Marco Alpegiani, et. al.

It is certified that error appears in the above-indentified patent and that said Letters Patent is hereby corrected as shown below:

Column 10, line 3, "40°" should read --40°C.--;

line 18, "700° C" should read --70° C--.

Signed and Sealed this

Fourteenth Day of January, 1997

Attest:

BRUCE LEHMAN

Attesting Officer    Commissioner of Patents and Trademarks